(12) United States Patent
Meeks

(10) Patent No.: US 7,286,229 B1
(45) Date of Patent: Oct. 23, 2007

(54) DETECTING MULTI-DOMAIN STATES IN PERPENDICULAR MAGNETIC MEDIA

(75) Inventor: Steven W. Meeks, Fremont, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 168 days.

(21) Appl. No.: 11/220,045

(22) Filed: Sep. 6, 2005

(51) Int. Cl.
G01J 4/00 (2006.01)

(52) U.S. Cl. .................................. 356/369; 356/448

(58) Field of Classification Search ............... 356/369, 356/445–448, 73, 237.1–237.6; 250/559.16–559.2
See application file for complete search history.

(56) References Cited

U.S. PATENT DOCUMENTS

| | | |
|---|---|---|
| 4,585,348 A | 4/1986 | Chastang |
| 4,870,631 A | 9/1989 | Stoddard |
| 4,873,430 A | 10/1989 | Juliana |
| 5,189,481 A | 2/1993 | Jann |
| 5,270,794 A | 12/1993 | Tsuji |
| 5,392,116 A | 2/1995 | Makosch |
| 5,416,594 A | 5/1995 | Gross |
| 5,610,897 A | 3/1997 | Yamamoto |
| 5,633,747 A | 5/1997 | Nikoonahad |
| 5,644,562 A | 7/1997 | de Groot |
| 5,798,829 A | 8/1998 | Vaez-Iravani |
| 5,864,394 A | 1/1999 | Jordan |
| 5,880,838 A | 3/1999 | Marx |
| 5,903,342 A | 5/1999 | Yatsugake |
| 5,985,680 A | 11/1999 | Singhal |
| 5,986,763 A | 11/1999 | Inoue |
| 5,995,226 A | 11/1999 | Abe |
| 6,031,615 A | 2/2000 | Meeks |
| 6,081,325 A | 6/2000 | Leslie |
| 6,130,749 A | 10/2000 | Meeks |
| 6,198,533 B1 | 3/2001 | Meeks |
| 6,229,610 B1 | 5/2001 | Meeks |
| 6,268,919 B1 | 7/2001 | Meeks |
| 6,392,749 B1 | 5/2002 | Meeks |
| 6,624,884 B1 | 9/2003 | Imaino |
| 6,665,078 B1 | 12/2003 | Meeks |
| 6,687,008 B1 | 2/2004 | Peale |
| 6,704,435 B1 | 3/2004 | Imaino |
| 6,717,671 B1 | 4/2004 | Meeks |
| 6,751,044 B1 | 6/2004 | Meeks |
| 6,757,056 B1 | 6/2004 | Meeks |
| 6,781,103 B1 | 8/2004 | Lane |
| 6,781,688 B2 * | 8/2004 | Kren et al. ............... 356/237.4 |
| 2002/0015146 A1 | 2/2002 | Meeks |
| 2002/0145740 A1 | 10/2002 | Meeks |
| 2002/0163634 A1 | 11/2002 | Meeks |
| 2003/0025905 A1 | 2/2003 | Meeks |
| 2004/0017561 A1 | 1/2004 | Meeks |
| 2004/0046959 A1 | 3/2004 | Meeks |
| 2004/0160604 A1 | 8/2004 | Meeks |
| 2004/0169850 A1 | 9/2004 | Meeks |
| 2004/0233419 A1 | 11/2004 | Meeks |
| 2005/0057747 A1 | 3/2005 | Meeks |

* cited by examiner

Primary Examiner—Layla G. Lauchman
Assistant Examiner—Tri Ton
(74) Attorney, Agent, or Firm—Caven & Aghevli LLC

(57) ABSTRACT

In one embodiment a system to detect multi-domain regions in the soft under layer of a perpendicular magnetic media comprises a radiation targeting assembly to target a polarized radiation beam onto a surface of a substrate covered by the soft under layer of a perpendicular magnetic media, a radiation collecting assembly that collects radiation reflected from the surface, a processor coupled to the first radiation collecting assembly, and a memory module coupled to the processor. The memory module comprises logic instructions which, when executed by the processor, configure the processor to record signal values from radiation reflected by the radiation beam at different positions on the surface and analyze the signal values to detect a region of multiple magnetic domains in the soft under layer of a perpendicular magnetic media.

18 Claims, 4 Drawing Sheets

US 7,286,229 B1

DETECTING MULTI-DOMAIN STATES IN PERPENDICULAR MAGNETIC MEDIA

BACKGROUND

The subject matter described herein relates to surface inspection techniques, and more particularly to detecting multi-domain states in perpendicular magnetic media.

Advances in magnetic recording media have led to the development of recording media that have a magnetic layer in which the axis of magnetization is perpendicular to the surface plane of the substrate, referred to sometimes as perpendicular magnetic media. Perpendicular magnetic media permit a high areal data density. Perpendicular magnetic media also have a soft magnetic under layer which is beneath the active magnetic layer. The purpose of the soft magnetic under layer is to provide a return path for the magnetic flux. However, the soft magnetic under layer of perpendicular magnetic media tends to be characterized by a low coercive field, and hence can readily fracture into multiple domains. Regions including multiple magnetic domain states cause magnetic noise when attempting to read data from a magnetic medium. Hence, it is desirable to detect regions that include multiple magnetic domain states in perpendicular magnetic recording media.

BRIEF DESCRIPTION OF THE DRAWINGS

The detailed description is described with reference to the accompanying figures.

SUMMARY

In one embodiment, a system to detect multi-domain regions in perpendicular magnetic media comprises a radiation targeting assembly to target a polarized radiation beam onto a surface of a substrate covered by a soft magnetic under layer, a radiation collecting assembly that collects radiation reflected from the surface, a processor coupled to the first radiation collecting assembly, and a memory module coupled to the processor. The memory module comprises logic instructions which, when executed by the processor, configure the processor to record signal values from radiation reflected by the radiation beam at different positions on the surface and analyze the signal values to detect a region of multiple magnetic domains in the soft magnetic under layer.

DETAILED DESCRIPTION

Described herein are exemplary systems and methods for detecting regions that include multiple magnetic domain states in perpendicular magnetic media. In the following description, numerous specific details are set forth to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

Figure 1:
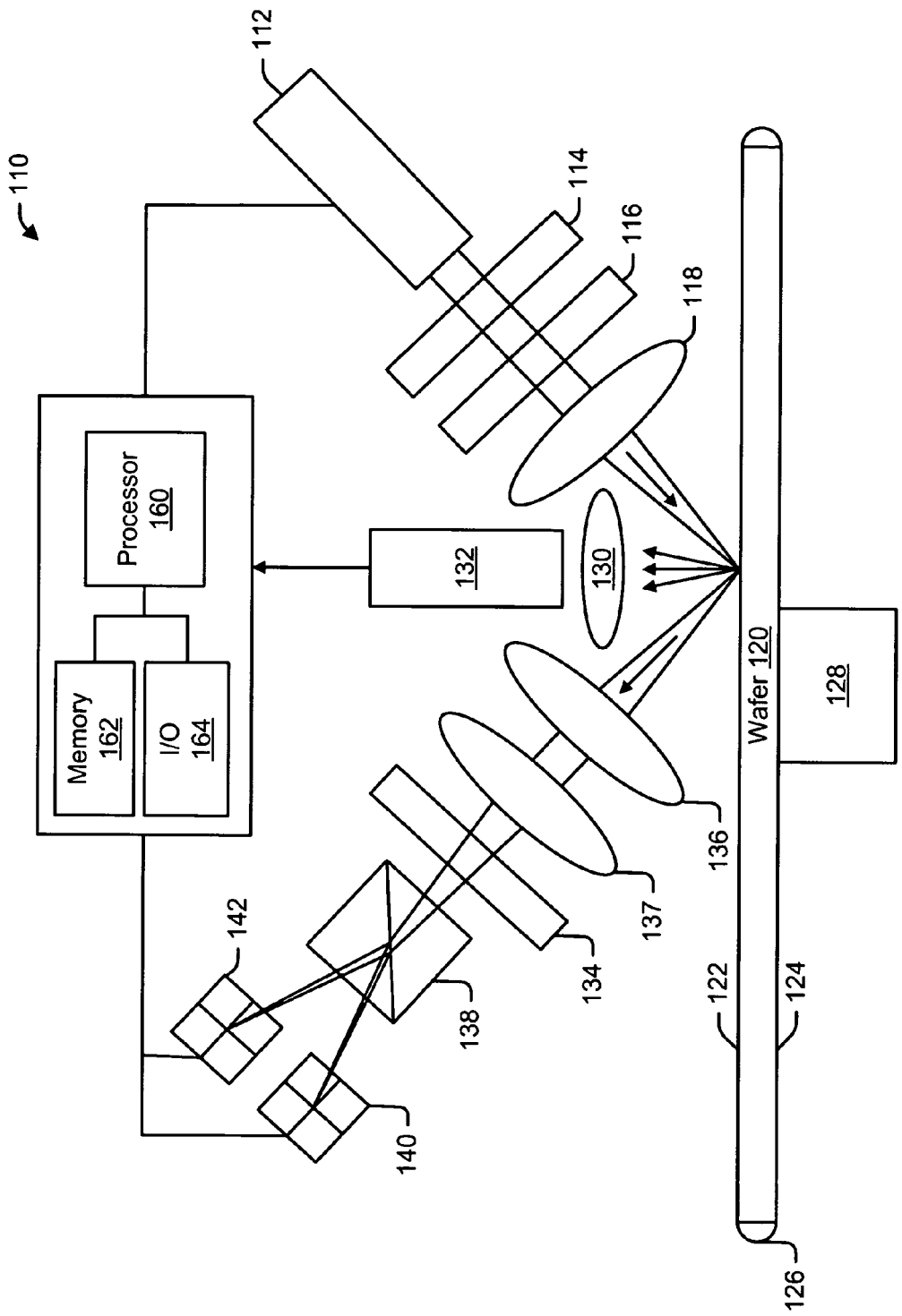
FIG. 1 is a schematic illustration of various optical components of an embodiment of an apparatus for wafer edge inspection.

FIG. 1 is a schematic illustration of one embodiment of an apparatus, sometimes referred to as an optical surface analyzer (OSA) for detecting multiple magnetic domain states in perpendicular magnetic media. Various optical testing components and techniques for surface inspection are described in U.S. Pat. Nos. 6,665,078, 6,717,671, and 6,757,056, and 6,909,500 to Meeks, et al., the disclosures of which are incorporated herein by reference in their entirety. Any of the assemblies and techniques described in these patents may be used in a surface analyzer for detecting multiple magnetic domain states in perpendicular magnetic media.

One embodiment may be adapted to perform film thickness measurements, surface roughness measurement, reflectivity measurement, magnetic imaging, and optical profiling using radiation in the optical spectrum. In alternate embodiments radiation outside the optical spectrum may be used. More particularly, FIG. 1 depicts an optics assembly capable of performing the above mentioned measurements that includes a combined reflectometer, scatterometer, phase shift microscope, magneto-optic Kerr effect microscope and optical profilometer. This embodiment is capable of detecting and classifying a wide variety of defects on a wafer or disk surface or wafer or disk edge, or near edge.

Wafer 120 includes an upper surface 122, a lower surface 124, and an edge surface 126, which may be substantially flat or curved when viewed in a cross-sectional profile. In the embodiment depicted in FIG. 1, the wafer edge surface is curved when viewed in cross-sectional profile.

A surface analyzer assembly 110 is positioned to direct radiation onto a surface of wafer 120. In the embodiment depicted in FIG. 1, surface analyzer assembly 110 includes a laser diode 112, an optional polarizer 114, an optional half-wave plate 116, and a focusing lens 118 for directing radiation onto a surface of wafer 120. These components target radiation from the laser diode onto the surface of wafer 120, and hence may be considered a radiation targeting assembly. In alternative embodiment polarizer 114 and half-wave plate 116 may be omitted.

Surface analyzer assembly 110 further includes a collecting lens 130 and a photomultiplier tube (PMT) 132. These components collect radiation scattered by the surface of the wafer 120, and hence may be considered a scattered radiation assembly. In alternative embodiments the PMT 132 and collecting lens 130 may be replaced with an integrating sphere or an ellipsoidal mirror together with a PIN photodiode or avalanche photodiode.

Surface analyzer assembly 110 further includes a collimating lens 136, an optional wobble reduction lens 137, a quarter wave plate 134, a Wollaston prism 138 rotated at 45 degrees to the plane of incidence, and two quadrant detectors 140, 142 available from Hamamatsu, Inc. In another embodiment, detectors 140 and 142 may be PIN photodetectors also available from Hamamatsu, Inc. The embodiment shown in FIG. 1 utilizes quadrant detectors so that the slope of the surface may be measured. The surface slope may be integrated to produce the surface profile. These components collect radiation reflected from the surface of wafer 120, and hence may be considered a reflected radiation assembly. The optional wobble reduction lens 137 may be embodied as a converging lens. In alternative embodiments the wobble reduction lens 137 and the collimating lens 136 may be combined into a single lens. The wobble reduction lens is chosen so that its focal length is substantially equal to the distance between wobble reduction lens 137 and the quadrant detectors 140 and 142. When this is done the surface slope measured at the quadrant detectors will be minimized. That is, the system will be most tolerant of wobble of the wafer. Another embodiment would position the detectors 140 and 142 at a distance slightly longer or shorter than the focal length of the wobble reduction lens 137. In this case the system would have some sensitivity to both wafer wobble and to surface slope.

In one embodiment surface analyzer assembly 110 uses a multi-mode, multi-wavelength laser diode 112 which is available from Rohm Co., LTD Kyoto, Japan as model number RLD-78 MV and a polarizer 114 which is adjusted for P polarization and improves the extinction ratio of the laser. The radiation may be of any wavelength. In one embodiment a 405 nm violet source available from Coherent, Inc may be implemented. In another embodiment a 635 nm source may be implemented. The mechanically rotatable half wave plate 116 is available from CVI Laser Corp. and can be used to rotate the polarization between 45 degrees, and P or S polarization's. Alternative techniques for rotating the polarization include rotating the laser diode 112 or to use a liquid crystal polarization rotator such as model LPR-100 available from Meadowlark Optics, Frederick, Colo. The latter embodiment has the advantage of being a purely electronic means of polarization rotation and as a result there is no possibility of beam movement when the polarization is rotated.

Focusing lens 118 creates a small spot on the surface of a wafer 120. The PMT 132 and collecting lens 130 are used to measure the scattered light for the purposes of computing the surface roughness, detecting pits or mounds, measuring debris, detecting stains, cracks, scratches, delaminations, blisters or corrosion on the disk or wafer 120 surface or edge 126 or near edge regions.

After reflecting from the disk, the beam passes through the collimating lens 136, the optional wobble reduction lens 137, and a quarter-wave plate 134. The beam is then polarization split with a Wollaston prism 138 available from CVI Laser Corp., for example, and each polarization component is detected with separate photodetectors 140, 142. The plane of the Wollaston prism (the plane of the S and P components) may be adjusted at substantially 45 degrees to the plane of incidence. The first mixed component of the beam (which includes both P and S components with respect to the plane of incidence) is directed to a detector 140 and the second mixed component (which includes both P and S components with respect to the plane of incidence) is directed to a second detector 142. In one embodiment the photodetectors 140, 142 may have a diffuser placed in front of them to reduce the residual position sensitivity of the photodiodes. The difference between the intensity measured by the photodetectors is proportional to the cosine of the phase difference between the first and second mixed components coming from the Wollaston prism. As a result this instrument can get different types of information when used in different modes.

When the polarization is adjusted to P, the P specular and P scattered light is measured resulting in sensitive measurements of carbon thickness (or any simple layer thickness) and carbon wear. The P specular signal is obtained by rotating the half wave plate 116 so that the polarization output from the half wave plate is P polarized. The P specular signal is given by the sum of the signal from 140 and 142. When the polarization is adjusted to 45 degrees (substantially between P and S polarization) the instrument is most sensitive to measurements of the phase change induced by changes in the thickness of the thin films on the disk or wafer surface. In the phase shift mode the instrument measures lubricant, carbon, or other film thickness changes on thin film disks or wafers. The phase shift is measured by taking the difference between the signals measured at 142 and 140. This gives an output that is proportional to the cosine of the phase difference between the first and second mixed components of the wave. The orientation of the quarter wave plate 134 is adjusted to optimize the sensitivity to lubricant, carbon wear, other film thickness changes or changes in phase due to the presence of defects. The individual components may also be measured; that is, the first and second mixed components of the 45 degrees polarized light. These are measured simultaneously with the phase shift and the scattered light.

When the half wave plate is rotated so that the polarization is adjusted to S polarization the instrument will be able to measure the S specular and the S scattered light and, as a result, obtain the surface roughness and other properties of the sample. The S specular signal is given by the sum of the signal from 140 and 142. In one embodiment, the surface analyzer shown in FIG. 1 may impinge radiation onto the surface 122 of wafer 120 at an angle of incidence that measures approximately 58 degrees, but angles greater or less than 58 degrees may also be used. The longitudinal or polar Kerr effect may be measured by operating the instrument in any of the linear polarization's, i.e., P, S or 45 degrees. The quarter wave plate 134 may be rotated to achieve maximum sensitivity to the magnetic pattern, which optimizes the Kerr effect signal. The orientation of the quarter wave plate which optimizes the Kerr effect may be different from that which optimizes for lubricant and carbon sensitivity. As a result the quarter wave plate is made to be removable, for example, so that two different and separately optimized plates can be used for the different applications. A different embodiment may include a miniature motor to rotate the orientation of the quarter wave plate so as to optimize the signal for the Kerr effect, lubricant, carbon or defect detection mode. Different polarizations may require a different quarter wave plate adjustment to achieve optimization. When in this mode the instrument functions as a Kerr effect microscope. In one embodiment the S polarization is used to image the longitudinal or polar Kerr effect. When the surface is imaged by the surface analyzer in S linear polarization the reflected light has its polarization converted to elliptical polarization, the major axis of which is rotated depending upon the orientation of the magnetization upon the thin film disk. This Kerr effect signal is detected by measuring the two signals coming from the polarization beam splitter and subtracting them. This will give a signal whose sign is related to the direction of the magnetization and whose amplitude is proportional to the magnetization.

The data collected by the scattered radiation collection assembly and the reflected radiation collection assembly is fed to a processing module that includes a processor 160, a memory module 162, and an I/O module 164. Processor module comprises logic instructions that enable the instrument described in FIG. 1 to simultaneously measure the profile (height and depth) of the surface, the S and P components of the reflectivity, the phase shift between the P and S waves and the scattered light. It is also capable of measuring the longitudinal or polar Magneto-optic Kerr effect.

The measurement of the phase shift between the S and P components of the optical wave requires a means to stabilize the long-term phase drift of the diode laser. This can be accomplished by the use of a reference mirror. The reference mirror may be embodied as a stable surface such as a gold mirror, a section of a thin film disk, or section of a silicon wafer. The reference mirror is calibrated when the instrument is first set up by measuring and recording the phase shift of the reference mirror. At times after the initial calibration of the instrument the reference mirror is measured prior to a measurement of the sample. Any deviation of the reference mirror reading from the initial reading is recorded and subtracted from the measurement of the sample readings. This insures that the phase shift reading from the surface under measurement will remain stable over time. The same procedure can also be applied to the measurement of the S specular and P specular signals. In this case when the instrument is calibrated the values of the P specular and S specular signals measured on the reference mirror are recorded and deviations from these values are used to correct the specular data. This removes any drift from the P and S specular signals.

Figure 2:
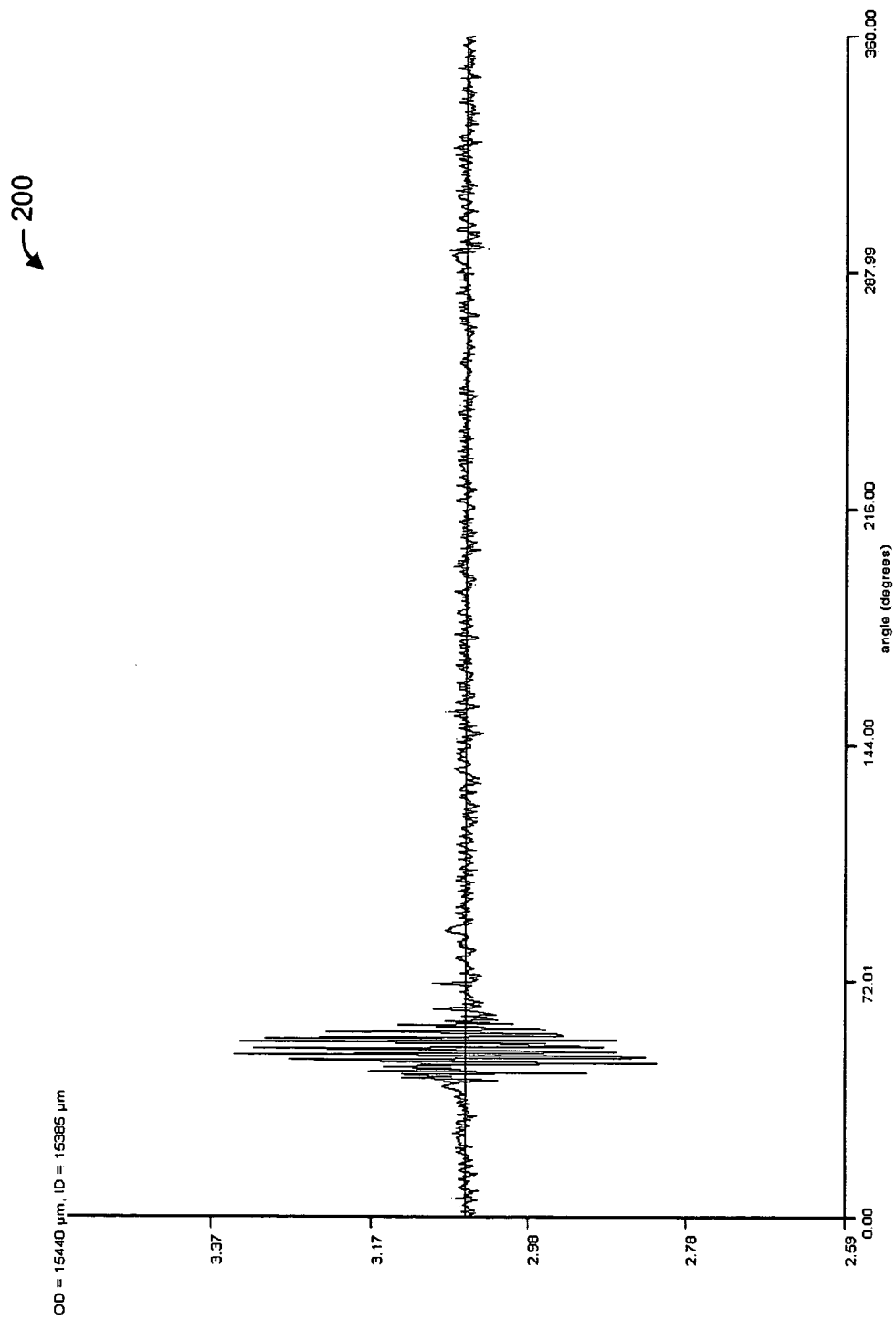
FIG. 2 graph illustrating magnetic noise due to a multi-domain state in perpendicular magnetic media.

In one embodiment, the surface analyzer depicted in FIG. 1 may be operated in a Kerr effect microscope mode to analyze a perpendicular magnetic media to detect regions in which the soft magnetic under layer has broken into multiple magnetic domains. FIG. 2 is a schematic illustration of a graph illustrating magnetic noise generated by the surface analyzer when scanning a single track of a magnetic disk comprising a soft magnetic under layer for a perpendicular magnetic media. In the embodiment depicted in FIG. 2, points on the surface of a perpendicular magnetic media are represented in polar coordinates; however Cartesian coordinates or any other coordinate system may be employed. Referring to FIG. 2, a Kerr effect microscope scan of a soft magnetic under layer for a perpendicular magnetic media reveals a baseline level of magnetic noise across the surface of the media and a region of high magnetic noise in the region between approximately 50 degrees and 70 degrees. This region of increased magnetic noise may be attributed to the soft under layer breaking into multiple magnetic domains.

Figure 3:
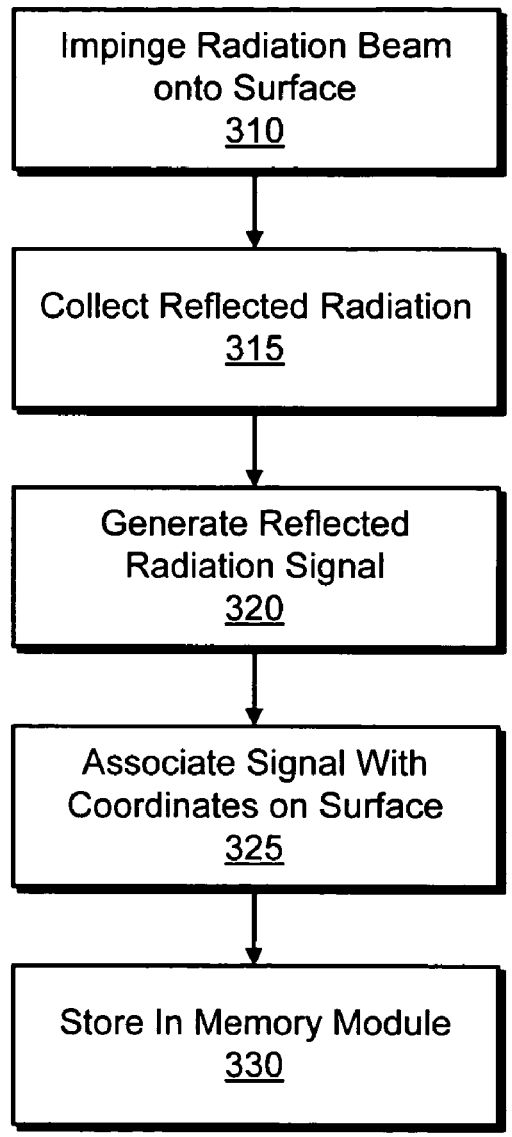
FIG. 3 is a flowchart illustrating operations in a method to detect a multi-domain state in a perpendicular magnetic media.

FIG. 3 is a flowchart illustrating operations in a method for detecting multiple magnetic domains. At operation 310 a first radiation beam is directed onto the surface 122 of wafer 120. The radiation beam is scanned across the surface of the wafer 120. In one embodiment, the wafer 120 may be rotated about a central axis, e.g., by spinning the wafer on a spindle, and the components may be translated along a radial axis, such that the entire surface 122 of wafer 120 is scanned. In alternate embodiments, the wafer may remain stationary and the components may be moved across the surface of wafer 120. Alternatively, the spinning wafer or disk may be translated in the radial direction beneath the fixed optical components.

In one embodiment, diode 112 may be adapted to direct S-polarized light onto the surface of wafer 220 at a wavelength of 780 or 655 nanometers. In another embodiment any optical wavelength (visible, UV or IR) may be used. In an alternate embodiment, radiation directing assemblies are adapted to direct both S-polarized light and P-polarized light onto the surface 122 of wafer 120. This may be accomplished, e.g., by including a rotatable half-wave plate to alternate between S-polarization and P-polarization.

At operation 315 radiation scattered from the surface of wafer 220 is collected. In operation 320 detectors 140, 142 collect a portion of the radiation reflected from the surface of wafer 220 and generate signals representative of characteristics of the radiation received. At operation 325 the signals generated by each detector 140, 142 are associated with coordinates on the surface 122 of wafer 120. In one embodiment, the surface 122 of wafer 120 may be mapped in (x, y) coordinates. In an alternate embodiment, the surface of wafer may be mapped in polar coordinates or any other suitable coordinate system. At operation 330 the signals and the associated coordinates are stored in a memory module such as, e.g., the memory module 162 depicted in FIG. 1.

Figure 4:
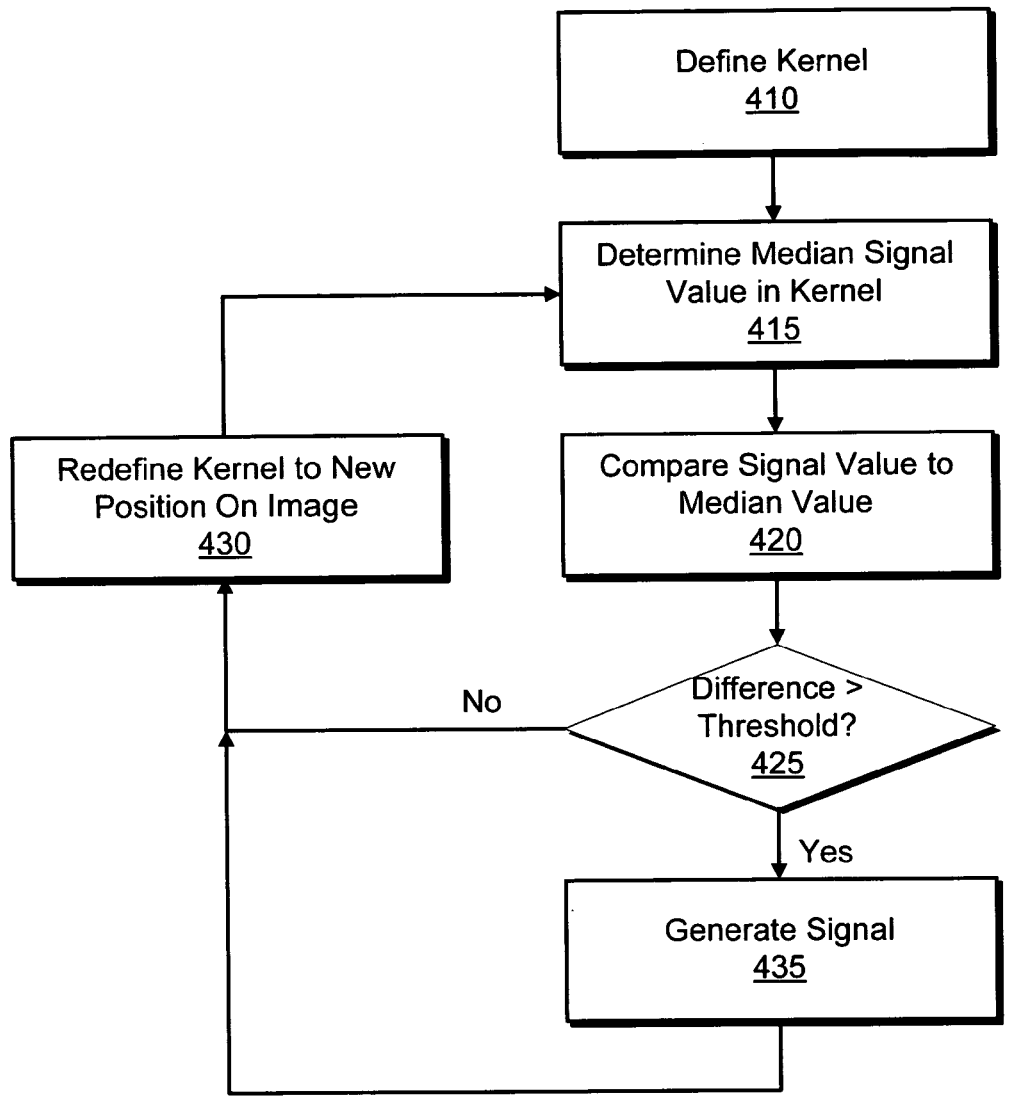
FIG. 4 is a flowchart illustrating operations in a method to detect a multi-domain state in a perpendicular magnetic media.

The signal values recorded in memory in operation 330 may be used to detect regions of multi-domain states in magnetic media on the surface of wafer 120. FIG. 4 is a flowchart illustrating operations in a method for detecting regions of multi-domain states in magnetic media. In one embodiment, the operations illustrated in FIG. 4 may be implemented as logic instructions stored in a computer-readable medium such as, e.g., the memory module 162 depicted in FIG. 1. At operation 410, a kernel is defined. As used herein, the term "kernel" refers to an array of signal value and coordinate data collected using the operations of FIG. 3. For example, a kernel may represent an array of signal values recorded over a section of the surface 122 of wafer 120. In one embodiment, the kernel may represent a moving window of signal values recorded over a length range between 30 micrometers and 5000 micrometers. In general, the shape of the kernel may be linear, square or any two-dimensional shape.

At operation 415 median signal values are determined using the data points recorded in the kernel defined in operation 410. In an alternate embodiment average values may be determined.

At operation 420 the signal values recorded at discreet data points in the kernel are compared to the median signal value for the kernel determined in operation 415. If, at operation 425, the difference between the value of the Kerr effect signal and the median value of the same Kerr effect signal calculated in operation 415 or the difference between the signal value and the median value calculated in operation 415 exceeds a threshold, then control passes to operation 435 and a signal is generated. The location of the signal is recorded in the memory module in operation 440. The signal indicates that a surface the region may include multiple magnetic domains. In one embodiment, the signal may be associated with the coordinates in a memory module such as, for example, the memory module 162 depicted in FIG. 1. By contrast, if at operation 425 the difference is less than a threshold, then control passes to operation 430 and the kernel is redefined to cover a new position on the image of the scanned surface. Control then passes back to operation 415 and a new median value is calculated for the kernel. This process is repeated until the entire disk (or a portion thereof) has been examined for multiple magnetic domains in the soft under layer of a perpendicular magnetic media.

In one embodiment the threshold may be static and may represent a factor of the median value calculated in operation 415. For example, the threshold may be set to a factor of 150% or 200% of the median value. In an alternate embodiment the threshold may be dynamic. After the signal is generated control passes back to operation 430 and a new kernel is defined. The operations of FIG. 4 may be repeated until the entire surface scan has been analyzed.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A system to detect multi-domain regions in a soft under layer of perpendicular magnetic media, comprising:
   a radiation targeting assembly to target a polarized radiation beam onto a surface of a substrate covered by a the soft under layer of a perpendicular magnetic media; and
   a radiation collecting assembly that collects radiation reflected from the surface;
   a processor coupled to the first radiation collecting assembly;
   a memory module coupled to the processor and comprising logic instructions which, when executed by the processor, configure the processor to:
      record signal values from radiation reflected by the radiation beam at different positions on the surface;
      analyze the signal values to detect a region of multiple magnetic domains in the soft under layer of a perpendicular magnetic media;
      establish a baseline noise value over a region of the surface;
      subtract a baseline noise value from a signal value generated at a specific location to obtain a noise-compensated signal value; and
      compare the noise-compensated signal value to a threshold.

2. The system of claim 1, wherein the radiation targeting assembly targets a beam of S-polarized radiation onto the surface.

3. The system of claim 1, further comprising logic instructions which, when executed by the processor, configure the processor to compare a signal value generated at a specific location with the baseline noise value over a region of the surface.

4. The system of claim 1, further comprising logic instructions which, when executed by the processor, configure the processor to redefine the region over which the baseline noise value is calculated.

5. The system of claim 1, wherein the radiation targeting assembly targets a beam of P-polarized radiation onto the surface.

6. A method to detect multi-domain regions in the soft under layer of a perpendicular magnetic media, comprising:
   targeting a polarized radiation beam onto a surface of a substrate covered by the soft under layer of a perpendicular magnetic media; and
   collecting radiation reflected from the surface;
   recording a signal value from radiation reflected from a plurality of different positions on the surface;
   analyzing the signal values to detect a region of multiple magnetic domains in the soft under layer of a perpendicular magnetic media wherein analyzing the signal value to detect a region of multiple magnetic domains in the soft under layer of a perpendicular magnetic media comprises: determining an average noise signal over the plurality of different positions on the surface; subtracting the average noise value from the signal value to obtain a first noise-compensated signal value; and comparing the first noise-compensated signal value to a threshold;
   generating, on a user interface, an output that indicates a region of multiple magnetic domains;
   wherein analyzing the signal values to detect a region of multiple magnetic domains in the soft under layer of a perpendicular magnetic media comprises:
      determining an average noise signal over the plurality of different positions on the surface; and
      comparing a signal value at a location on the surface with the average noise value.

7. The method of claim 6, wherein:
the radiation beam comprises S-polarized light.

8. The method of claim 6, wherein the plurality of different positions on the surface represents a two-dimensional area on the surface.

9. The method of claim 6, wherein analyzing the signal values to detect a region of multiple magnetic domains in the soft under layer of a perpendicular magnetic media comprises:
   determining a median noise signal over the plurality of different positions on the surface; and
   comparing a signal value at a location on the surface with the average noise value.

10. The method of claim 6, wherein analyzing the signal value to detect a region of multiple magnetic domains in the soft under layer of a perpendicular magnetic media comprises:
    determining a median noise signal over the plurality of different positions on the surface;
    subtracting the median noise value from the signal value to obtain a first noise-compensated signal value; and
    comparing the first noise-compensated signal value to a threshold.

11. The method of claim 6, wherein:
the radiation beam comprises P-polarized light.

12. A system to detect multi-domain regions in a soft under layer of perpendicular magnetic media, comprising:
    a radiation targeting assembly that targets a polarized radiation beam onto a surface of a substrate covered by the soft under layer of a perpendicular magnetic media; and
    a radiation collecting assembly that collects radiation reflected from the surface;
    a processor coupled to the first radiation collecting assembly;
    a memory module coupled to the processor and comprising logic instructions which, when executed by the processor, configure the processor to:
       record signal values from radiation reflected by the radiation beam at different positions on the surface;
       generate a noise-compensated signal from the signal values; and
       use the noise-compensated signal and the signal values to detect a region of multiple magnetic domains in the soft under layer of a perpendicular magnetic media.

13. The system of claim 12, wherein the radiation targeting assembly targets a beam of S-polarized radiation onto the surface.

14. The system of claim 12, further comprising logic instructions which, when executed by the processor, configure the processor to establish a baseline noise value over a region of the surface.

15. The system of claim 12, further comprising logic instructions which, when executed by the processor, configure the processor to compare the noise-compensated signal value to a threshold.

16. The system of claim 15, further comprising logic instructions which, when executed by the processor, configure the processor to redefine the region over which the baseline noise value is calculated.

17. The system of claim 14, wherein the threshold corresponds to a multiple of the baseline noise value.

18. The method of claim 6, wherein analyzing the signal values to detect a region of multiple magnetic domains in the soft under layer of a perpendicular magnetic media comprises:
 determining an average noise signal over the plurality of different positions on the surface; and
 comparing a signal value at a location on the surface with the average noise value.

* * * * *